US00PP20039P2

(12) United States Plant Patent
Celestian

(10) Patent No.: US PP20,039 P2
(45) Date of Patent: May 26, 2009

(54) ***CALLIANDRA* HYBRID 'CASCADA DESIERTICA'**

(50) Latin Name: *Calliandra californica*
Varietal Denomination: Cascada Desiertica

(75) Inventor: Sarah Celestian, Waddell, AZ (US)

(73) Assignee: Desert Tree Farm, Phoenix, AZ (US)

( * ) Notice: Subject to any disclaimer, the term of this patent is extended or adjusted under 35 U.S.C. 154(b) by 0 days.

(21) Appl. No.: 12/012,671

(22) Filed: Feb. 4, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—S. B. McCormick Ewoldt
(74) *Attorney, Agent, or Firm*—Townsend and Townsend and Crew LLP

(57) ABSTRACT

The present invention is a new and unique variety of *Calliandra californica.* This *Calliandra* occurred as a mutant seedling and is designated 'Cascada Desiertica' as a cultivar name and is trademarked as SARITA™. 'Cascada Desiertica' differs from the parent plants as well as other plants of this genus by exhibiting a strongly prostrate growth habit.

3 Drawing Sheets

Genus and species: The *Calliandra* cultivar of this invention is botanically identified as *Calliandra californica.*

Variety denomination: The variety denomination is 'Cascada Desiertica'.

BACKGROUND OF THE INVENTION

'Cascada Desiertica' originated as a mutant seedling found in a block of seedlings from open-pollinated *Calliandra californica* seedlings grown at a nursery in Phoenix, Ariz. This plant was selected as a single plant for its prostrate growth habit and has been maintained by asexual propagation. SARITA™ is a trade mark applied to the variety to indicate the source of origin thereof.

BRIEF SUMMARY OF THE INVENTION

Presented is a new variety of the genus *Calliandra,* discovered in Phoenix, Ariz. This new variety exhibits a strongly prostrate growth habit, up to 30 cm, which is in stark contrast to the upright growth habit, up to 2 m, of the parent plants as well as other plants of this genus. While the prostrate growth habit distinguishes the new variety 'Cascada Desiertica' from the parent plant, this new variety maintains other characteristics and environmental tolerances associated with the wild-type *Calliandra californica.*

Asexual propagation of 'Cascada Desiertica' has been performed in Phoenix, Ariz. by cuttings, and several generations have been established. The selected prostrate growth habit is stable from generation to generation.

BRIEF DESCRIPTION OF THE DRAWINGS

'Cascada Desiertica' is illustrated by the accompanying photographs, which show a typical 18 month old specimen of the plant and of plant parts, with such colors of the photograph being as true to those of the plant as can be reasonably obtained from conventional photographic procedures.

DETAILED DESCRIPTION OF THE INVENTION

Figure 1:
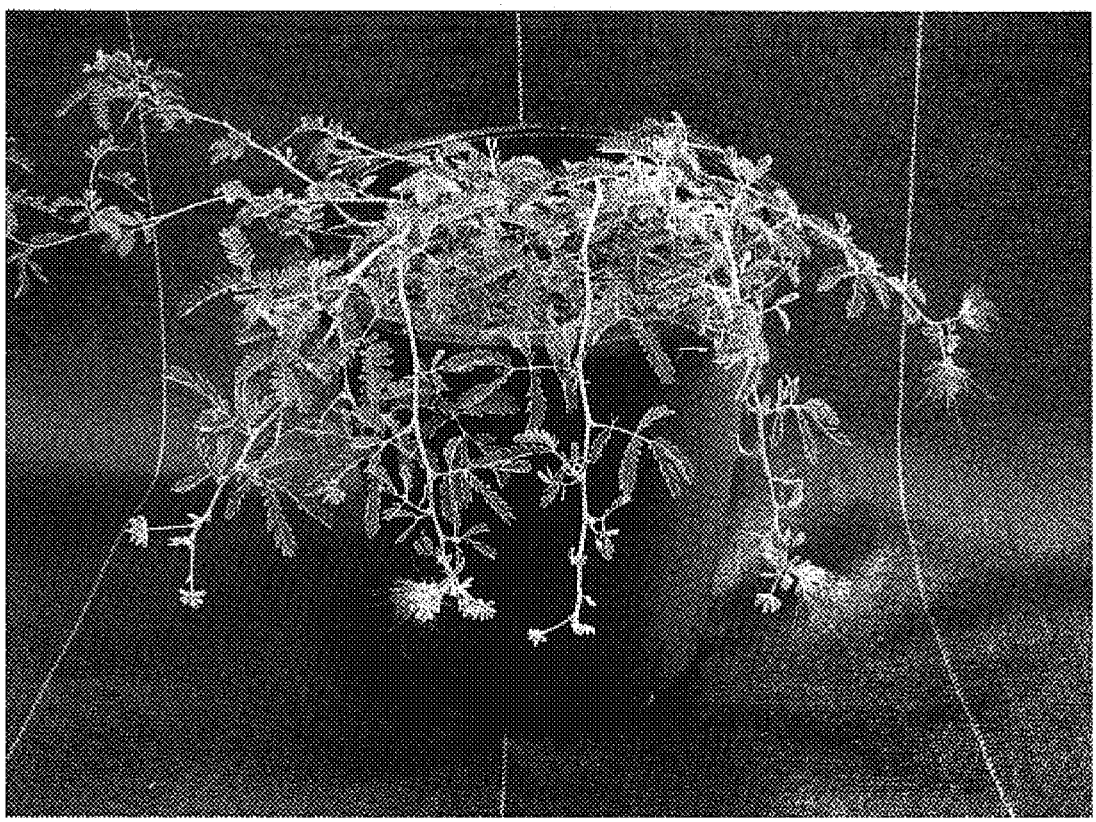
FIG. 1 shows branches, leaves and flowers of the 'Cascada Desiertica' plant as appearing in a greenhouse environment.
Figure 2:
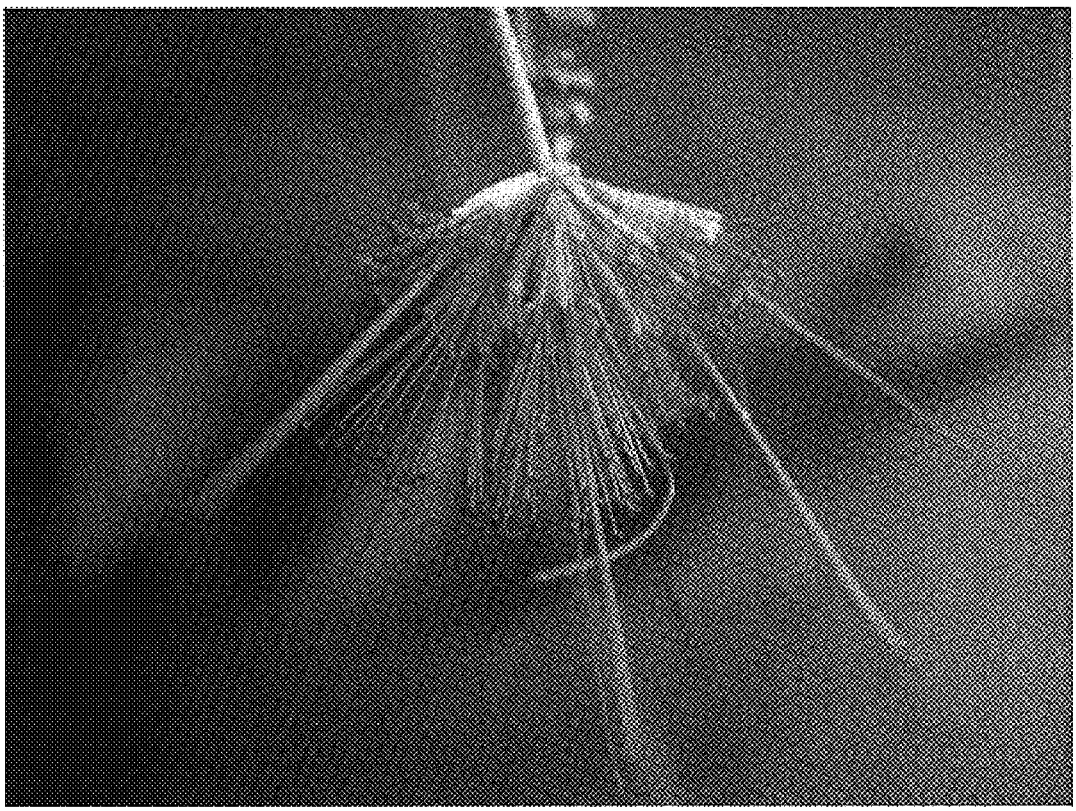
FIG. 2 shows a close-up view of the flower of the plant 'Cascada Desiertica' appearing in a greenhouse environment.
Figure 3:
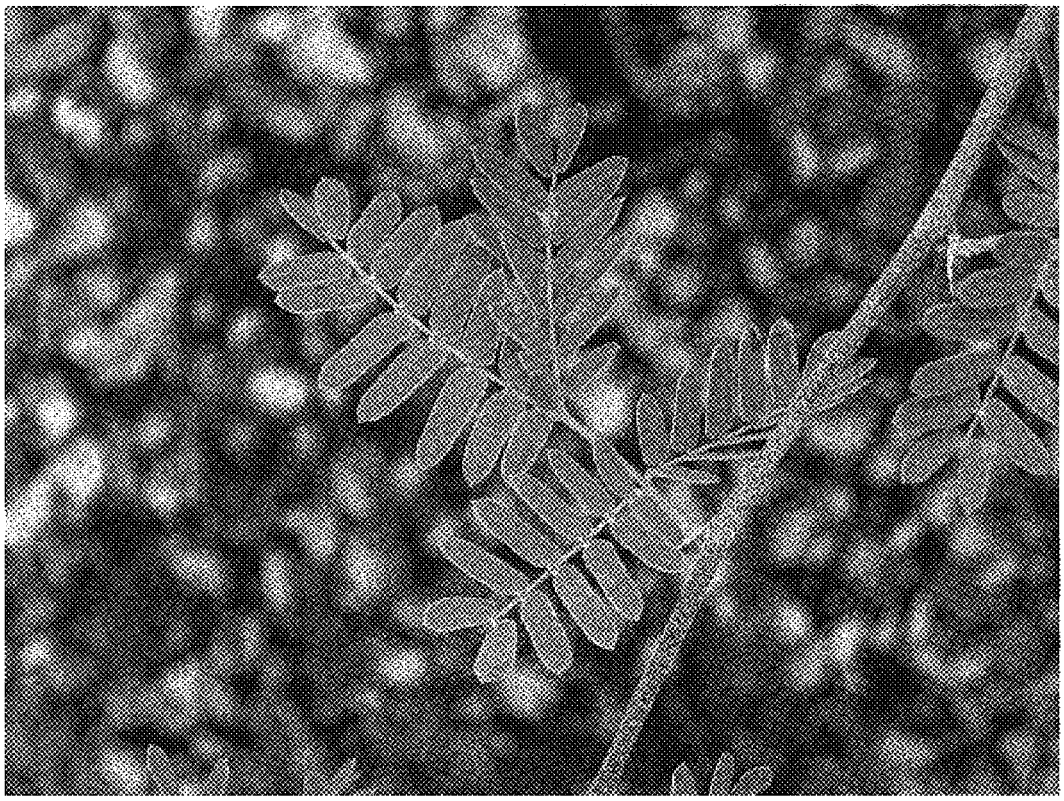
FIG. 3 shows a close-up view of the leaf of the plant 'Cascada Desiertica' appearing in a greenhouse environment.

The following is a detailed description of the new *Calliandra* 'Cascada Desiertica', based upon observation of plants grown in Phoenix, Ariz. The color designations being according to The R.H.S. Colour Chart published by The Royal Horticultural Society of London, England.

Botanical Description:

*Classification.*—*Calliandra californica.*
*Plant age.*—18 months.
*Plant form.*—Groundcover.
*Plant height.*—To 30 cm.
*Plant width.*—To 1.5 m.
*Plant growth habit.*—Multibranched, sprawling shrub with heavy sidebranching.
*Stem/lateral branch diameter.*—1.5–5 mm.
*Stem/lateral branch internode.*—2–5 cm.
*Leaf arrangement.*—Alternate, often 2 or 3 at nodes.
*Stipules.*—Narrowly triangular-elongate, 2–5 mm.
*Petiole length.*—7–28 mm.
*Petiole diameter.*—0.5–1.5 mm.
*Petiole color.*—RHS Yellow Green Group from 146A and 146C, including 146A and 146C.
*Leaf shape.*—Evenly bipinnate with the number of pinnae varying between 1, 2 or 3 pairs of pinnae.
*Leaf length.*—Pinnae: 20–50 mm., lower (proximal) pair usually shorter.
*Leaf width.*—40–90 mm.
*Leaflets.*—5–10 pairs, 5–13 mm long, 2–4 mm wide, oblong-elliptic.
*Leaflet base.*—Unequal.
*Leaflet apex.*—Mucronate.

*Leaflet pubescence.*—Finely appressed below, glabrous above.

*Leaflet margin.*—Entire.

*Leaflet color.*—Upper surface— RHS Green Group from 138A and 137B, including 138A and 137B, uniform over surface; underside— RHS Yellow Green Group from 137A and 137C, including 137A and 137C, uniform over surface.

*Rachis.*—RHS Yellow Green Group from 146B and 146D, including 146B and 146D, uniform.

Description of the flower:

*Inflorescence type.*—Axillary heads.

*Peduncle length.*—22–33 mm.

*Peduncle diameter.*—0.8–1.0 mm.

*Peduncle color.*—RHS Green Group from 146B and 146D, including 146B and 146D.

*Flower number.*—8–12.

*Calyx.*—5 toothed.

*Calyx shape.*—Tubular-funnelform.

*Calyx length.*—0.5–1.5 mm.

*Calyx width.*—1–1.5 mm.

*Calyx pubescence.*—Sparsely pubescent with closely appressed fine hairs on outer surface.

*Calyx color.*—RHS Yellow Green Group from 152D and 153B, including 152D and 153B, aging to mottled RHS Red Group from 45A and 46B, including 45A and 46B.

*Corolla shape.*—Funnelform, with 5 lobes.

*Corolla height.*—6–7 mm including lobes.

*Corolla lobe length.*—1–1.5 mm. recurving with age.

*Corolla diameter.*—2.5–3.5 mm. near widest part.

*Corolla lobes.*—Acute, 1–1.5 nm long, with entire margins. The corolla is fused.

*Corolla color.*—At base RHS Yellow Green Group from 154B and 154D, including 154B and 154D, grades to mottled RHS Red Group from 46A and 46C, including 46A and 46C.

*Corolla pubescence.*—Finely pubescent with closely appressed fine hairs on outer surface.

*Pistil.*—1 pistil per flower, copious nectar at base.

*Style length.*—17–25 mm.

*Style color.*—RHS Red Group from 45A and 45C, including 45A and 45C.

*Stigma.*—Capitate, glabrous.

*Stigma width.*—0.2–0.3 mm.

*Filament number.*—17–26, fused at base.

*Filament length.*—Free portion — 12–16 mm.

*Filament color.*—RHS Red Group from 45B and 45D, including 45B and 45D.

*Pollen.*—Scarce.

*Pollen color.*—Yellowish, too small to use color chart.

*Bud peduncle length.*—1–33 mm.

*Bud peduncle diameter.*—0.5–1 mm.

*Bud peduncle color.*—RHS Yellow Green Group from 146C and 146B, including 146C and 146B.

*Bud number.*—8–12.

*Bud color* (*corolla in bud*).—RHS Yellow Green Group from 144D and 145A, including 144D and 145A.

*Bud shape.*—Clavate (club shaped, gradually widening toward apex).

*Bud length.*—1–8 mm.

*Bud width.*—1–2.5 mm.

*Bud vestiture.*—Appressed, strait hairs, <1 mm long, more abundant toward tips of corolla lobes in bud.

*Fragrance.*—No noticeable fragrance detected.

*Fruit.*—Dehiscent, 2-valved capsule, margins thickened.

*Seeds.*—Indistinguishable from other species in the genus *Calliandra*.

What is claimed is: A new and distinct cultivar of *Calliandra californica* plant having the characteristics substantially as described and illustrated herein.

1. A new and distinct cultivar of *Calliandra californica* plant having the characteristics substantially as described and illustrated herein.

* * * * *